US010181371B1

(12) United States Patent
Tse et al.

(10) Patent No.: US 10,181,371 B1
(45) Date of Patent: Jan. 15, 2019

(54) APPARATUS FOR MAGNETOSTRICTIVE SENSOR FOR GUIDED-WAVE-BASED INSPECTION, AND ITS ASSOCIATED SYSTEM AND METHOD

(71) Applicant: City University of Hong Kong, Kowloon (HK)

(72) Inventors: Peter Wai Tat Tse, Nam Shan Yuen (HK); Zhou Fang, Sanming (CN)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 0 days.

(21) Appl. No.: 15/691,938

(22) Filed: Aug. 31, 2017

(51) Int. Cl.
   *H01F 5/00* (2006.01)
   *G01N 27/82* (2006.01)
   *G01L 1/12* (2006.01)

(52) U.S. Cl.
   CPC .............. *H01F 5/003* (2013.01); *G01L 1/125* (2013.01); *G01N 27/82* (2013.01)

(58) Field of Classification Search
   CPC .......... H01F 5/003; G01L 1/125; G01N 27/82
   See application file for complete search history.

(56) References Cited

U.S. PATENT DOCUMENTS

| 2007/0241849 | A1* | 10/2007 | Heinrich | F16F 15/005 335/215 |
|---|---|---|---|---|
| 2008/0272852 | A1* | 11/2008 | Six | H03H 9/02259 331/154 |
| 2018/0058208 | A1* | 3/2018 | Song | E21B 41/0085 |
| 2018/0190085 | A1* | 7/2018 | Khoshkava | B06B 1/045 |

FOREIGN PATENT DOCUMENTS

CN 107607623 A * 1/2018

OTHER PUBLICATIONS

Tse P., Liu X., Liu Z., Wu B., He C., and Wang X., 'An Innovative Design of Using Flexible Printed Coil for Magnetostrictive-based Longitudinal Guided Wave Sensor in Steel Strand Inspection', Small Materials and Structures. 20 (2011) 055001, May 2011 (12pp), doi: 10.1088/0964-1726/20/51055001.
Fang Z., Tse P. and Wei Y., 'Axial magnetized patch for efficient transduction of longitudinal guided wave and defect identification in concrete-covered pipe risers', NDT & E International, submitted May 22, 2017.

(Continued)

*Primary Examiner* — Francis C Gray
(74) *Attorney, Agent, or Firm* — Renner Kenner Greive Bobak Taylor & Weber

(57) ABSTRACT

An apparatus for a magnetostrictive sensor for guided-wave-based inspection includes a flexible body with a conductor arranged to receive an alternating current for generating a magnetic field. During operation, the flexible body is arranged to be attached to an object to be inspected in such a way that a first part of the conductor arranged to generate a magnetic field parallel to a longitudinal direction of the object is arranged to surround the object and a second part of the conductor arranged to generate a magnetic field perpendicular to the longitudinal direction of the object is disposed away from the object.

26 Claims, 11 Drawing Sheets
(11 of 11 Drawing Sheet(s) Filed in Color)

(56) References Cited

OTHER PUBLICATIONS

Tse P., Chen J. and Wan X., 'Guided-waves Technique for Inspecting the Health of Wall-covered Building Risers', 41st Annual Review of Progress on Quantitative Non-destructive Evaluation, Selected Papers, vol. 34, pp. 676-685, editors D. Chimenti & L Bond, AIP Publishing, New York, 2015. ISBN 978-0-7354-1292-7.

Tse P., Rostami J. and Chen J., 'Novel Techniques to Reveal Defects Hidden in Wall-covered Building Risers', the 7th Greater Pearl River Delta (GPRD) Conference on Building Operation and Maintenance—Smart Facilities Operation and Maintenance, Dec. 6, Hong Kong, pp. 146-155 pages.

Tse P., Liu X., Wang X., and Wang D., 'A Novel and Flexible Design of Magnetostrictive Sensor for Strand/Rope Defect Inspection', Proceedings of the ASME 2011 International Design Engineering Technical Conferences & Computers and Information in Engineering Conference (IDETC/CIE 2011), Aug. 28-31, 2011, Washington, DC, USA.

Liu Z., Fan J., Hu Y., He C., and Wu B., 'Torsional mode magnetostrictive patch transducer array employing a modified planar solenoid array coil for pipe inspection', NDT & E International, vol. 69, pp. 9-15, Jan. 2015.

Liu et al, Torsionalmodemagnetostrictivepatchtransducerarrayemploying a modified planarsolenoidarraycoilforpipeinspection https://www.sciencedirect.com/science/article/pii/S0963869514001157?via%3Dihub.

Liu Z., Hu Y., Fan J., Yin W., Liu X, He C, et al., 'Longitudinal mode magnetostrictive patch transducer array employing a multi-splitting meander coil for pipe inspection', NDT & E International, vol. 79, pp. 30-37, Apr. 2016.

\* cited by examiner

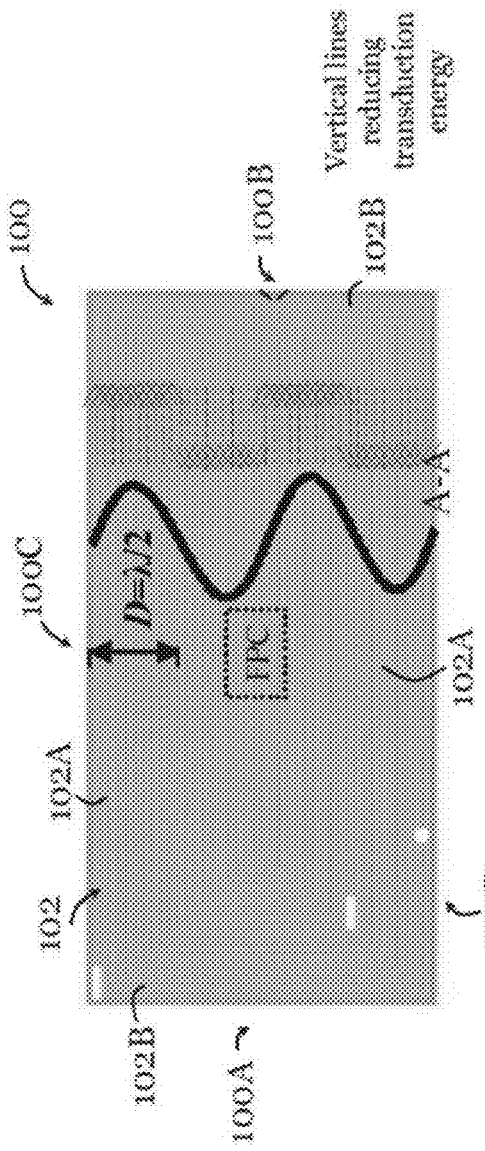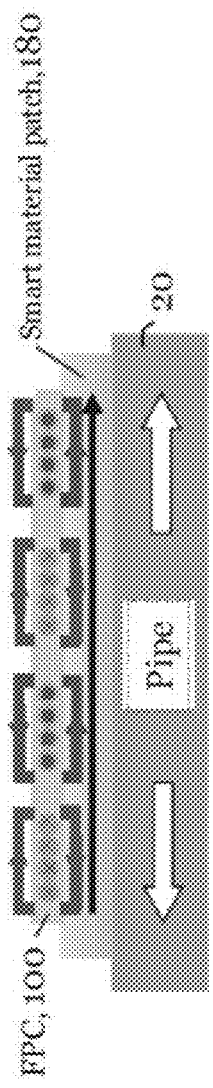
Figure 2A
Figure 2B

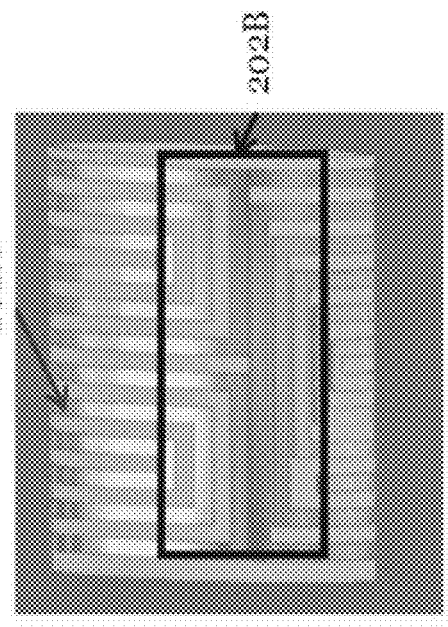
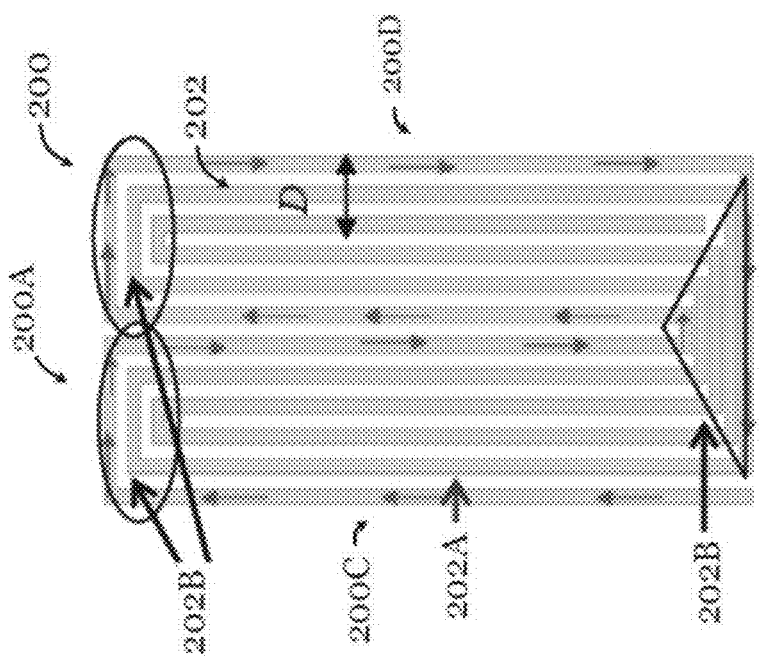
Figure 3B
Figure 3A

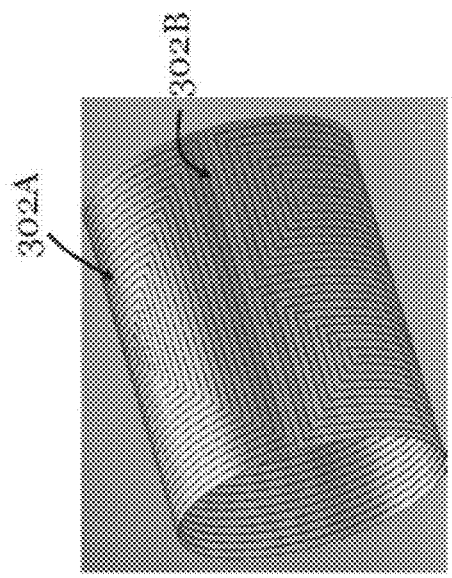
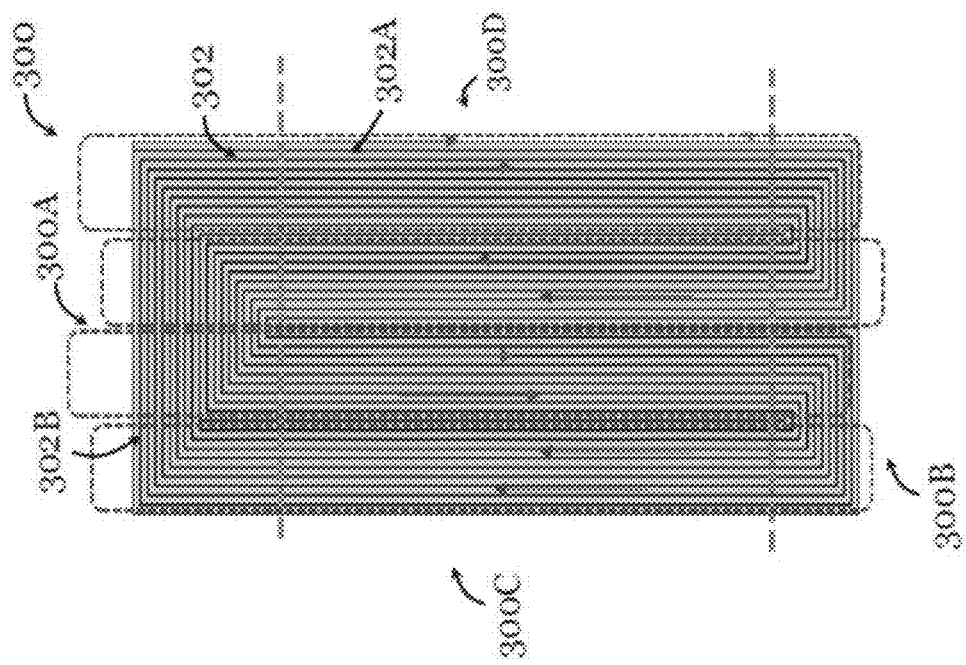
Figure 3D
Figure 3C

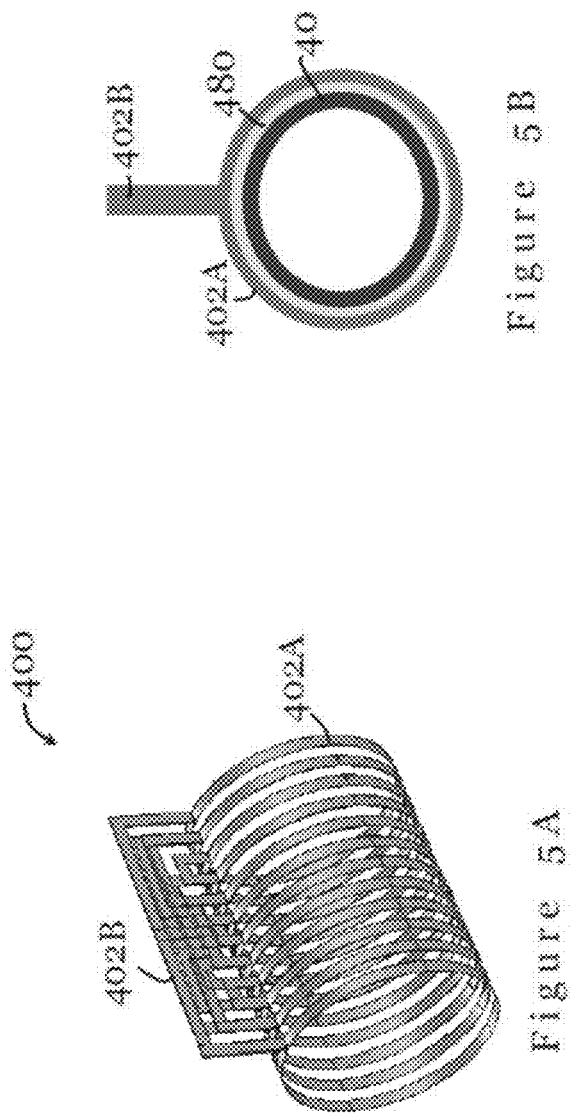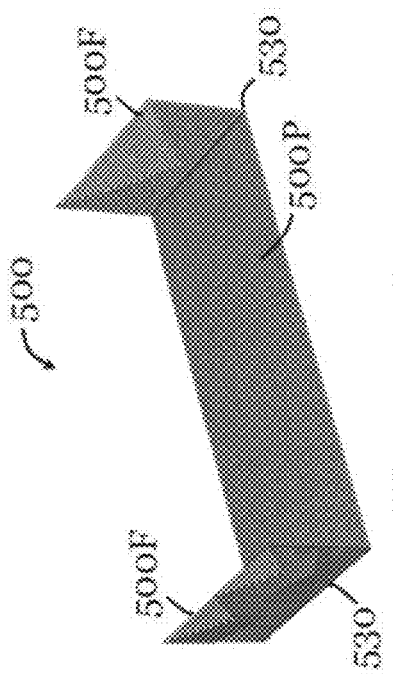

APPARATUS FOR MAGNETOSTRICTIVE SENSOR FOR GUIDED-WAVE-BASED INSPECTION, AND ITS ASSOCIATED SYSTEM AND METHOD

TECHNICAL FIELD

The invention relates to an apparatus for use in a magnetostrictive sensor for guided-wave-based inspection of the integrity and corrosion extent of objects. More particularly, although not exclusively, the invention relates to an apparatus for use in guided-wave-based inspection of the integrity and corrosion extent of buried, concealed, and covered structures such as pipes.

BACKGROUND

Guided-wave-based defect inspection is known for its long-range inspection ability and high sensitivity in detecting small defects in objects. In major applications, guided-wave-based defect inspection is used for detecting cracks and corrosion that may occur in structures like pipes, rods, strands, cables, etc.

Existing sensors used for creating (exciting) and receiving guided-wave generally are magnetostrictive sensors that include a hard sensing coil for generating a necessary magnetic field for exciting the desired guided-wave. FIG. 1A shows a conventional hard coil-based magnetostrictive sensor 10 arranged around a wire strand 1. The magnetostrictive sensor 10 includes three consecutive groups of hard coils 11A, 11B, 11C disposed along the wire strand 1 and each surrounding the wire strand 1. The hard coils 11A-11C are formed by hard coil wires. The longitudinal length of each group is equal to half of the wavelength of the excited guided-wave mode. The first and third groups of hard coils 11A, 11C are wound in a first direction (e.g., clockwise), and the second group 11B disposed between the first and third groups 11A, 11C is wound in a second, opposite direction (e.g., anti-clockwise), as shown in FIG. 1B. The magnetostrictive sensor 10 also includes two sets of permanent magnets 12 disposed around the wire strand 1. The first set of permanent magnets formed by three equally-angularly spaced magnets is arranged at the end of the first group of coil 11A, the second set of permanent magnetics formed by three equally-angularly spaced magnets is arranged at the end of the third group of coil 11C. The hard coils 11A-11C are arranged between the two sets of permanent magnets 12. Yokes 13 are arranged to connect magnets of the two sets 12 that are at substantially the same angular position. As shown in FIG. 1A, three yokes 13 are provided and they are equally angularly spaced around the wire strand. Referring to FIG. 1B, the magnets and yoke generate a uniformly distributed bias magnetic field on the steel strand. The coils on the other hand, generate dynamic magnetic fields. At the instance shown in FIG. 1B, the first and third groups of coils 11A, 11C generate magnetic field that has the same direction as the bias magnetic field while the second group of coil 11B generate a magnetic field that has an opposite detection to the bias magnetic field. The bias magnetic field and the dynamic magnetic fields are both substantially parallel to a longitudinal axis of the strand 1. Through the interactions between the bias and dynamic magnetic fields, the desired longitudinal guided-wave mode can be excited in the strand 1 for inspection.

While this type of hard coil-based magnetostrictive sensor is useful in some applications, they are usually bulky, and are only suitable for use in steel strands of predetermined size. Mounting of the coils or the magnets may be difficult if the other objects to be measured do not have a suitably sized free end. Also, applications are also limited to use in inspection of metallic objects or structures.

SUMMARY OF THE INVENTION

In accordance with a first aspect of the invention, there is provided an apparatus for a magnetostrictive sensor for guided-wave-based inspection, comprising: a flexible body with a conductor arranged to receive an alternating current for generating magnetic field, wherein during operation the flexible body is arranged to be attached to an object to be inspected in such a way that a first part of the conductor arranged to generate a magnetic field parallel to a longitudinal direction of the object is arranged to surround the object; and a second part of the conductor arranged to generate a magnetic field perpendicular to the longitudinal direction of the object is disposed away from the object. By attaching the flexible body to the object in such a way, the second part is further away from the object than the first part, uniformity and evenness of magnetic field generated by the apparatus is improved, and a more reliable and effective inspection can be performed.

Preferably, the flexible body comprises first and second ends; the first part comprises a plurality of first sections arranged adjacent and substantially parallel to each other, each extending between the first and second ends; and the second part comprises at least one second section for connecting the plurality of first sections.

Preferably, the plurality of first sections each extends at least 50% of a length between the first and second ends. More preferably, the plurality of first sections each extends at least 75% of a length between the first and second ends. In one example, the plurality of first sections each extends at least 90% of a length between the first and second ends. The plurality of first sections may all optionally extend the same length. The plurality of first sections may optionally extend parallel to an edge of the body. Preferably, the plurality of first sections are spaced apart equally.

Preferably, the conductor is a single, continuous conductor. The first sections and second section may be connected to form a continuous strip.

In one embodiment of the first aspect, the plurality of first sections form at least two adjacent groups, each having at least one first section; wherein during operation when an alternating current is supplied to the conductor, current direction in the first sections of two adjacent groups are opposite.

In one embodiment of the first aspect, the plurality of first sections form at least two adjacent groups, each having a plurality of adjacent first sections; wherein during operation when an alternating current is supplied to the conductor, current direction in the first sections of the same group is the same while current direction in the first sections of the two adjacent groups are opposite.

In one embodiment of the first aspect, the plurality of first sections form at least four adjacent groups, each having a plurality of adjacent first sections; wherein during operation when an alternating current is supplied to the conductor, current direction in the first sections of the same group is the same while current direction in the first sections of any two adjacent groups are opposite.

Preferably, a width spanned by the first sections of each group is substantially the same. Preferably, a width D spanned by the first sections of each group is equal to:

$$\frac{V_p}{2f_0}$$

where $f_0$ is a centre frequency of the magnetostrictive sensor, and $V_p$ is a phase velocity of an excited longitudinal guided-wave.

Preferably, the conductor comprises a plurality of second sections disposed at both the first and second ends. Each of the plurality of second sections may comprise at least one part that extends generally perpendicular to the plurality of first sections.

Preferably, the flexible body comprises a flexible printed coil.

In one embodiment of the first aspect, the apparatus further comprises a fastener for holding the second part away from the object.

Preferably, the flexible body is arranged to be wrapped around a smart material layer on the object during operation in such a way that the first part surrounds the smart material layer and the second part is disposed away from the smart material layer Preferably, the object is substantially cylindrical. In some embodiments, the object may be of other shapes, such as cuboidal, prismatic, cubical, etc. In one embodiment of the first aspect, the object comprises any one of: a pipe, a tube, a rod, a strand, and a cable. The object may be made of plastic or metal. For example, the object may be drainage pipe, oil pipe, gas pipe, etc., in buildings, underground, oil fields, subsea area, etc.

In accordance with a second aspect of the invention, there is provided a system for use in guided-wave-based inspection, comprising: a flexible smart material layer arranged to be attached to an object to be inspected; an apparatus with a flexible body having a conductor arranged to receive an alternating current for generating magnetic field, wherein during operation the flexible body is arranged to be attached to the smart material layer attached to the object in such a way that a first part of the conductor arranged to generate a magnetic field parallel to a longitudinal direction of the smart material layer is arranged to surround the smart material layer; and a second part of the conductor arranged to generate a magnetic field perpendicular to the longitudinal direction of the smart material layer is disposed away from the smart material layer. The system at least partly forms a magnetostrictive sensor.

Preferably, the flexible body comprises first and second ends; the first part comprises a plurality of first sections arranged adjacent and substantially parallel to each other, each extending between the first and second ends; and the second part comprises at least one second section for connecting the plurality of first sections.

Preferably, the system further comprises a magnetic field generator for generating a static magnetic field in one or both of the object to be inspected and the smart material layer.

In one embodiment of the second aspect, the system further comprises a fastener for holding the second part away from the flexible smart material layer.

In one embodiment of the second aspect, the system further comprises a data acquisition unit arranged to be connected with the smart material patch for acquiring detection signals received.

Preferably, the flexible body comprises a flexible printed coil.

Preferably, the object is substantially cylindrical. In some embodiments, the object may be of other shapes, such as cuboidal, prismatic, cubical, etc. In one embodiment of the first aspect, the object comprises any one of: a pipe, a tube, a rod, a strand, and a cable. The object may be made of plastic or metal. For example, the object may be drainage pipe, oil pipe, gas pipe, etc., in buildings, underground, oil fields, subsea area, etc.

In one embodiment of the second aspect, the apparatus with the flexible body is the apparatus in accordance with the first aspect of the invention.

In accordance with a third aspect of the invention, there is provided a method for guided-wave-based inspection, comprising: (1) providing an apparatus for a magnetostrictive sensor for guided-wave-based inspection, comprising a flexible body with a conductor arranged to receive an alternating current for generating magnetic field; and (2) attaching the flexible body to an object to be inspected in such a way that a first part of the conductor arranged to generate a magnetic field parallel to a longitudinal direction of the object is arranged to surround the object and a second part of the conductor arranged to generate a magnetic field perpendicular to the longitudinal direction of the object is disposed away from the object.

Preferably, the method further comprises attaching a flexible smart material layer to the object to be inspected prior to attaching the flexible body to the object.

Preferably, the method further comprises providing an alternating current to the conductor for generation of a magnetic field.

Preferably, the method further comprises magnetizing the smart material layer to form a static magnetic field therein.

Preferably, the flexible body comprises a flexible printed coil.

Preferably, the object is substantially cylindrical. In some embodiments, the object may be of other shapes, such as cuboidal, prismatic, cubical, etc. In one embodiment of the first aspect, the object comprises any one of: a pipe, a tube, a rod, a strand, and a cable. The object may be made of plastic or metal. For example, the object may be drainage pipe, oil pipe, gas pipe, etc., in buildings, underground, oil fields, subsea area, etc.

Preferably, the apparatus for the magnetostrictive sensor is the apparatus in accordance with the first aspect of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the invention will now be described, by way of example, with reference to the accompanying drawings in which:

FIG. 2A is a schematic diagram of a flexible printed circuit in accordance with one embodiment of the invention;

FIG. 2B is a schematic cross-sectional diagram of a magnetostrictive sensor formed by the flexible printed circuit in FIG. 2A and a smart material layer, for use in guided-wave-based inspection;

FIG. 3A is a schematic diagram of a flexible printed circuit in accordance with another embodiment of the invention;

FIG. 3B is a schematic diagram showing the flexible printed circuit in FIG. 3A wrapped into a first configuration;

FIG. 3C is a schematic diagram of a flexible printed circuit in accordance with yet another embodiment of the invention;

FIG. 3D is a schematic diagram showing the flexible printed circuit in FIG. 3C wrapped into a first configuration;

FIG. 5A is a simplified schematic diagram showing conductor layout of a flexible printed circuit wrapped into a second configuration in a preferred embodiment of the invention;

FIG. 5B is a simplified schematic diagram showing an arrangement of the flexible printed circuit in FIG. 5A in the second configuration during operation in one embodiment of the invention;

FIG. 5C is a simplified schematic diagram showing conductor layout of a flexible printed circuit in one embodiment of the invention;

DETAILED DESCRIPTION OF THE PREFERRED EMBODIMENT

The inventors of the invention have devised, through research, experiments, and trials, that a magnetostrictive sensor can be made based on a flexible printed circuit or coils, instead of hard coils. The inventors have devised that such magnetostrictive sensor should include two main parts: a first part with a thin sheet of smart material and a second part with a flexible printed coil circuit formed by a thin and flexible sheet of printed coils. The flexible printed coil circuit, being thin and bendable, can be easily wrapped around any structure or object to be inspected. Such flexible-printed-coil-based magnetostrictive sensor can be used for inspection of structure such as pipes and cables. The inventors have also realized that the desired guided-wave signal is generated by magnetostrictive effect, and so this type of flexible-printed-coil-based magnetostrictive sensor can only be used for inspecting object or structure made of ferromagnetic material.

The inventors of the invention also have devised, through research, experiments, and trials, a type of flexible-printed-coil-based magnetostrictive sensor that can be applied for inspection of object or structure made of plastic (e.g., PVC), in addition to use in inspection of object or structure made of metal.

Figure 1A:
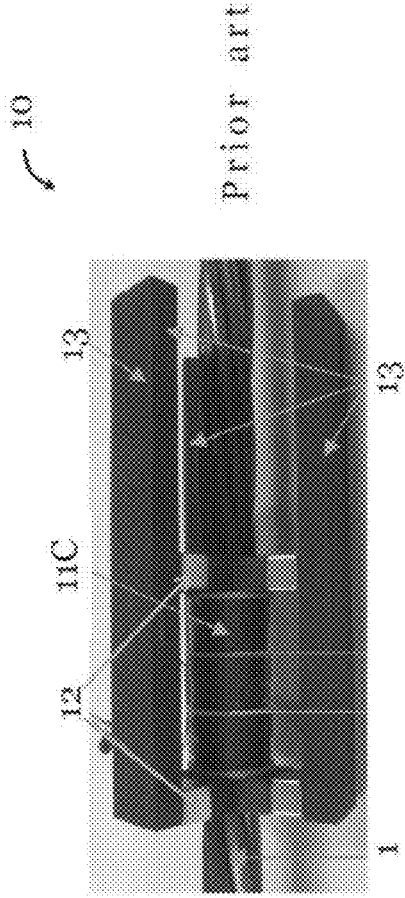
FIG. 1A is a picture showing a conventional hard-coil-based magnetostrictive sensor arranged around a wire strand.
Figure 1B:
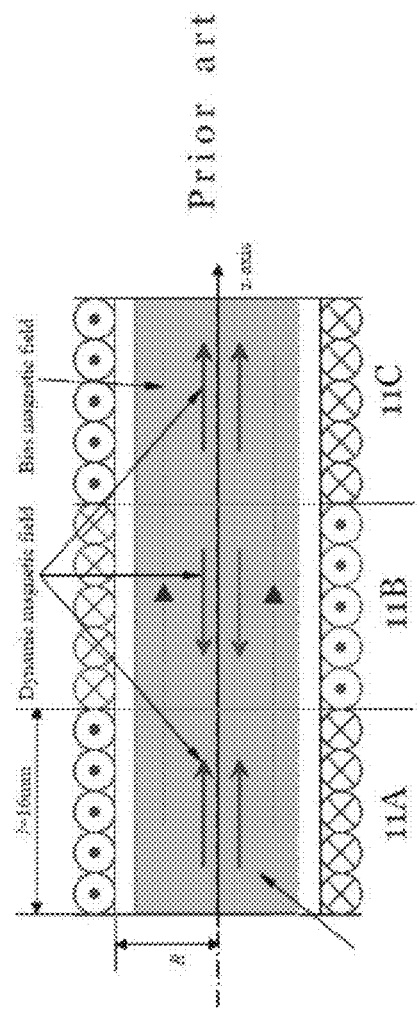
FIG. 1B is a schematic cross section for illustrating the operation of the conventional hard-coil-based magnetostrictive sensor of FIG. 1A.

FIG. 2A shows plan view of a flexible printed circuit 100, in the form of a flexible printed coil, which can be used to form a magnetostrictive sensor in one embodiment of the invention. The flexible printed coil 100 is preferably thin and bendable. The flexible printed coil 100 comprises a generally rectangular body formed by a flexible substrate (not clearly shown) and a conductor 102 printed or arranged on the substrate. The body includes a first end 100A and a second end 100B, and opposing first side 100C and second side 100D extending between the first and second ends 100A, 100B. The conductor 102 is arranged to receive an alternating electric current (connections not shown). The conductor 102 may be a single, continuous conductor. As shown in FIG. 1A, the conductor 102 includes multiple first sections 102A arranged adjacent and substantially parallel to each other. Each of the first sections 102A extends generally parallel to the first and second sides 100C, 100D, between the first and second ends 100A, 100B. The first sections 102A may have different lengths, and they may be equally spaced. In one embodiment, the first sections 102A each extend at least 50% of a length between the first and second ends 100A, 100B, and preferably at least 75% of a length between the first and second ends 100A, 100B. The conductor 102 further includes multiple second sections 102B, at both the first and the second ends 100A, 100B, for connecting the first sections 102A. The second sections 102B extend generally perpendicular to the first and second sides 100C, 100D.

The first sections 102A are arranged such that multiple first sections 102A together form a group. FIG. 2A shows four groups. Each group contains multiple first sections 102A which are arranged such that when an alternating current is supplied to the conductor 102, current in the first sections 102A of the same group flow in the same direction (see arrows in FIG. 2A) while current in first sections 102A of an adjacent group flow in opposite directions (see arrows in FIG. 2A). Preferably, a width D spanned by the first sections 102A of each group is substantially the same.

FIG. 2B show part of a magnetostrictive sensor 150 formed by the flexible printed coil 100 of FIG. 2A and a smart material layer 180 in one embodiment of the invention. The magnetostrictive sensor 150 is arranged around an object 20 (e.g., a hollow pipe) to be inspected. For simplicity, only the upper-half cross section of the pipe 20 in shown in FIG. 2B. The smart material layer 180 is preferably magnetostrictive, and is formed of a thin sheet that can be bent like the flexible printed coil circuit 100. The smart material layer 180 may be connected with a data acquisition system (not shown) for recording or analysing signals received by the smart material layer 180. In application, both the smart material layer 180 and the flexible printed coil 100 are wound around the pipe 20. More particularly, the smart material layer 180 is first wound around the pipe 20, and then the flexible printed coil 100 is wound around the smart material layer 180 and hence the pipe 20. Preferably, the smart material layer 180 and the flexible printed coil 100 both conform to the outer contour of the object around which they wrap. The wrapping is preferably tight.

In operation, a static magnetic field and a dynamic magnetic field are simultaneously applied (excited) to the magnetostrictive sensor 150 to generate a desired guided-wave signal using magnetostrictive effect. In one embodiment, to generate a static magnetic field, a magnetic field generator (not shown), e.g., a magnet, is arranged to create a magnetic field in the smart material layer 180. The magnet may be a permanent magnet, and it preferably uniformly magnetizes the smart material layer 180 along its entire axial length. The smart material layer 180, upon being magnetized, generates a static magnetic field. In one embodiment, to generate a dynamic magnetic field, an alternating current is continuously provided to the conductor 102 of the flexible printed coil 100. As shown in FIG. 2B, each of the four groups of coils (formed by the first sections 102A) generates a magnetic field, with opposite magnetic fields for adjacent groups due to the difference in direction of current flow in adjacent groups.

As shown in FIG. 2B, the direction of the generated static magnetic field is generally parallel to the direction of the dynamic magnetic field. These enable excitation of longitudinal guided-waves mode (also called "L-mode") and propagation of such guided-waves along a longitudinal axis of the pipe 20. When an "L-mode" is excited, the generated magnetostrictive effect is applied to the smart material layer 180, causing it to deform longitudinally (i.e., axially). Such deformation of the smart material layer 180 consequently generates a longitudinal guided-wave in the pipe body 20. The "L-mode" guided-wave will then propagate along the pipe 20. Preferably, the guided-waves propagate in both directions along the pipe 20. During propagation of the wave, when there is discontinuity inside the pipe body, such as a crack or a corroded area on or in the pipe 20, part of the guided-wave energy will be reflected towards the sensor. The reflected guided-wave signal will be received by the smart material layer 180 used to excite the guided-wave signal and then recorded by the data acquisition system in connection with the smart material layer 180. As the velocity of the propagating guided-wave is known, and the time of the reflected guided-wave signal received by the sensor can be detected, the distance or location of the discontinuity in the pipe can be determined.

FIG. 3A show a flexible printed circuit 200 in accordance with another embodiment of the invention. The flexible printed circuit 200 in FIG. 3A is largely the same as the flexible printed circuit 100 in FIG. 2A, except for the number of first and second sections, and the spacing of the first and second sections. In FIG. 3A, the conductor 202 of the flexible printed circuit 200 comprises multiple first sections 202A arranged adjacent and substantially parallel to each other. Each first section 202A extends generally parallel to the first and second sides 200C, 200D, between the first and second ends 200A, 200B. The conductor further includes multiple second sections 202B, at both the first and the second ends 200A, 200B, for connecting the first sections 202A. The second sections 202B extend generally perpendicular to the first and second sides 200C, 200D.

Same as in FIG. 2A, the first sections 202A may form groups. The width of each group is denoted by D. In the invention, width D is determined is based on the following equation:

$$f_0 = \frac{V_p}{\lambda}$$

where $f_0$ is an centre frequency of magnetostrictive sensor, $V_p$ is the phase velocity of the excited L-mode, and $\lambda$ is the wavelength. Since $2D=\lambda$, the distance between two adjacent groups is equal to half of the wavelength of the excited guided-wave mode. As the half wavelength effect and the time delay to generate the L-mode by the successive group is also half of the wavelength, the aggregated L-mode waveform will result in a higher amplitude temporal waveform (as illustrated in FIG. 2A: the sinusoidal waveform in black colour).

Thus, the provision of multiple (in the present example, four) groups of first sections 202A, having equal width D, in the sheet of flexible printed coil can excite higher amplitude for the guided-wave signal. Since the higher the excited guided-wave signal, the larger the sensitivity in detecting small discontinuity or defect, the present embodiment substantially improves detection sensitivity.

Although a flexible printed coil 200 with a conductor 202 having multiple groups of first sections 202A is preferred, when the coil 200 is wrapped around in the first configuration as shown in FIG. 3B, it may create some undesirable effect on the generated magnetic field. In particular, as shown in FIG. 3A, the directions of alternating current flowing in first sections 202A of two adjacent groups are opposite. To enable a change in direction for the alternating current, the flexible printed coil 200 must contain second sections 202B at least partly at an angle to (or even perpendicular to) the first sections. These second sections 202B may be undesirable, as explained below.

FIG. 3C show another flexible printed circuit 300 in accordance with another embodiment of the invention. The flexible printed circuit 300 in FIG. 3C is largely the same as the flexible printed circuit 200 in FIG. 3A. In FIG. 3C, the conductor 302 of the flexible printed circuit 300 comprises multiple first sections 302A arranged adjacent and substantially parallel to each other. Each first section 302A extends generally parallel to the first and second sides 300C, 300D, between the first and second ends 300A, 300B. The conductor further includes multiple second sections 302B, at both the first and the second ends 300A, 300B, for connecting the first sections 302A. The second sections 302B extend generally perpendicular to the first and second sides 300C, 300D.

Same as in FIG. 3A, the first sections 302A may form groups. As shown this embodiment includes four groups (see dotted lines). The width of each group is denoted by D, which is determined is based on the following equation:

$$f_0 = \frac{V_p}{\lambda}$$

where $f_0$ is an centre frequency of magnetostrictive sensor, $V_p$ is the phase velocity of the excited L-mode, and $\lambda$ is the wavelength. Since $2D=\lambda$, the distance between two adjacent groups is equal to half of the wavelength of the excited guided-wave mode. As the half wavelength effect and the time delay to generate the L-mode by the successive group is also half of the wavelength, the aggregated L-mode waveform will result in a higher amplitude temporal waveform.

The provision of multiple groups of first sections 302A, each having equal width D, in the sheet of flexible printed coil can excite higher amplitude for the guided-wave signal. Since the higher the excited guided-wave signal, the larger the sensitivity in detecting small discontinuity or defect, the present embodiment substantially improves detection sensitivity.

Although a flexible printed coil 300 with a conductor 302 having multiple groups of first sections 302A is preferred, when the coil 300 is wrapped around in the first configuration as shown in FIG. 3D, it may create some undesirable effect on the generated magnetic field. In particular, as shown in FIG. 3C, the directions of alternating current flowing in first sections 302A of two adjacent groups are opposite. To enable a change in direction for the alternating current, the flexible printed coil 300 must contain second sections 302B at least partly at an angle to (or even perpendicular to) the first sections. These second sections 302B may be undesirable in some applications, as explained below.

Figure 4:
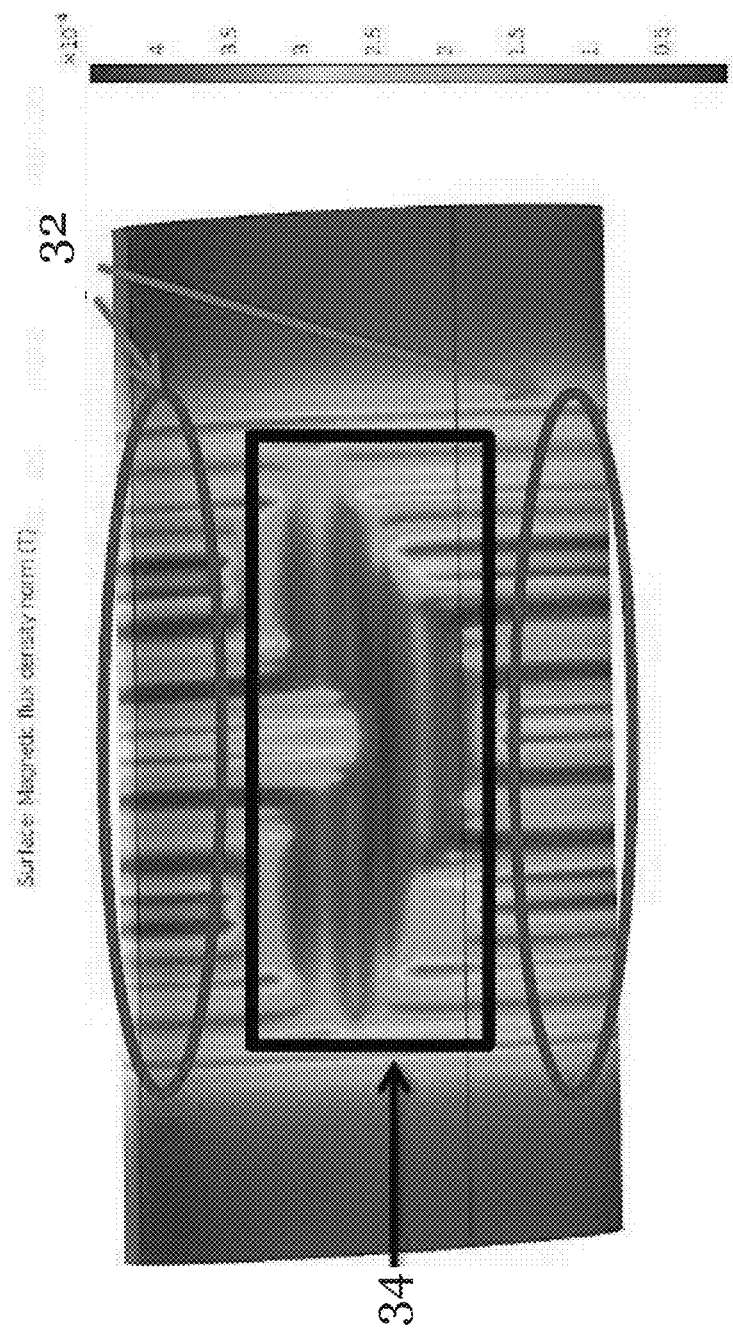
FIG. 4 is a simulated plot showing the normalized surface magnetic flux density (T) of the wrapped flexible printed circuit in FIG. 3B.

FIG. 4 shows a simulated plot showing the normalized surface magnetic flux density (T) of the flexible printed circuit in FIG. 3B. As shown in FIG. 4, when the coil is wrapped in the first configuration, the first sections (circumferential coils) generate an axial magnetic field 32 for exciting the L-mode guided-wave signal. The second sections (axial coils) generate a magnetic field 34 in the circumferential direction. This circumferential magnetic field 34 interferes with the useful axial magnetic field 32, and does not contribute to form the desired excitation of L-mode guided-wave signal.

In other words, the second sections (axial coils) interfere with the magnetic fields 32 induced by the first sections (circumferential coils) of flexible printed coil sheet. FIG. 4 shows the non-uniform distribution of magnetic field 34 created (in the black rectangular box). The non-uniform magnetic field 34 not only substantially weakens the excited guided-wave signal, but may also trigger excitation of unwanted modes such as the Flexural modes (also called "F-modes"), making the analysis of the reflected guided-wave signals difficult.

FIGS. 5A and 5B shows a flexible printed circuit 400 wrapped into a second configuration in a preferred embodiment of the invention. In FIG. 4A, only the conductor layout is provided; and the circuit or coil 400 is provided in a second wrapped configuration. The flexible printed circuit 400 in this embodiment may be similar to that in FIGS. 2A and 3A. Like the flexible printed circuits 100, 200 in FIGS. 2A and 3A, the flexible printed circuit 400 in this embodiment also include, prior to wrapping, a flexible body (not shown) having first and second ends and a conductor 402 arranged to receive an alternating current for generating magnetic field during inspection. In this embodiment, the conductor 402 also has multiple first sections 402A arranged adjacent and substantially parallel to each other and multiple second sections 402B for connecting the first sections 402A. As shown in FIG. 5A, in the second configuration, the flexible body is arranged such that at least part of the first sections 402A surrounds the object to be inspected and the second sections 402B are disposed away from the object. In other words, only the first sections 402A surround the object, and the second sections 402B are further away from the object than the first sections 402A. As shown in FIG. 5B, the first sections 402A (circumferential coils) form a cylindrical part for surrounding a pipe 40 to be inspected, and the second sections 402B (axial coils) form a radial portion extending away from the cylindrical part formed by the first sections 402A (circumferential coils). By arranging all second sections 402B (axial coils) away from the object, the non-uniform magnetic field generated by the second sections 402B (axial coils) will have very little effect on or even not affect the uniform magnetic field induced by the first sections 402A (circumferential coils). Optionally, a fastener (not shown) may be arranged to hold the second sections 402B away from the first sections 402A (circumferential coils) and hence away from the object to be inspected. The fastener may be a chemical fastener (e.g., glue) or a mechanical fastener (e.g., clips).

FIG. 5C shows a flexible printed circuit 500 in one embodiment of the invention, in an unwrapped form. The circuit 500 may include two folded portions 500F at two ends of a planar portion 500P. In this embodiment, the folded portions 500F extend at an angle of around 90 degrees to the planar portion 500P. In other embodiments, the folded portions 500F may extend at a different angle. The folded portions 500F preferably contain the second sections which may generate non-uniform magnetic field when the circuit is wrapped edge-to-edge. In this example, the circuit 500 may be folded so that the two folding lines 530 coincide during operation such that the second sections are disposed away from the object to be measured.

To compare the effectiveness of the arrangement in FIGS. 5A and 5B with the arrangement in FIG. 3B, simulation tests were conducted.

Figure 6B:
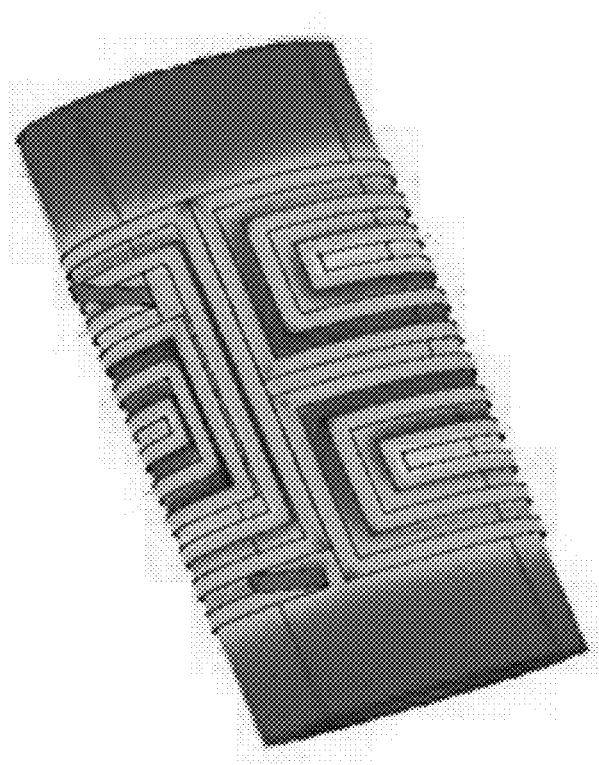
FIG. 6B is a simulated plot showing distribution of magnetic flux density in the flexible printed circuit of FIG. 5A wrapped in the first configuration.
Figure 6A:
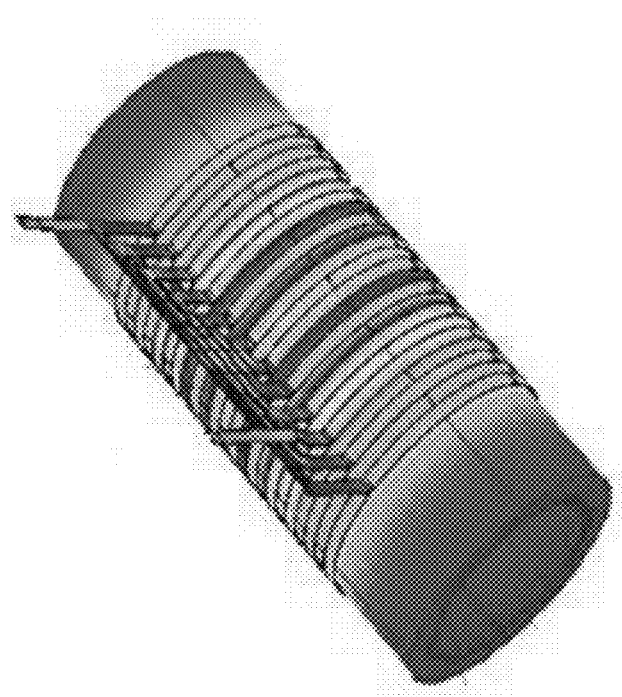
FIG. 6A is a simulated plot showing distribution of magnetic flux density in a flexible printed circuit wrapped in the second configuration.

FIGS. 6A and 6B are simulated plots showing distribution of magnetic flux density in a flexible printed circuit wrapped in the second configuration (FIG. 6A) and in the first configuration (FIG. 6B). As shown in FIG. 6A, by arranging the second sections (axial coils) whose interference negatively influence the generation of uniform magnetic field away from the first sections (circumferential coils), the distribution of magnetic flux density around the pipe is more uniform. In FIG. 6B, due to the arrangement of second sections (axial coils) on the object, the distribution of magnetic field is uneven and the flux density is substantially weakened. Also, the coil in FIG. 6A can excite L-mode guided-wave signal at larger amplitude as illustrated by deep yellow colour.

Figure 7B:
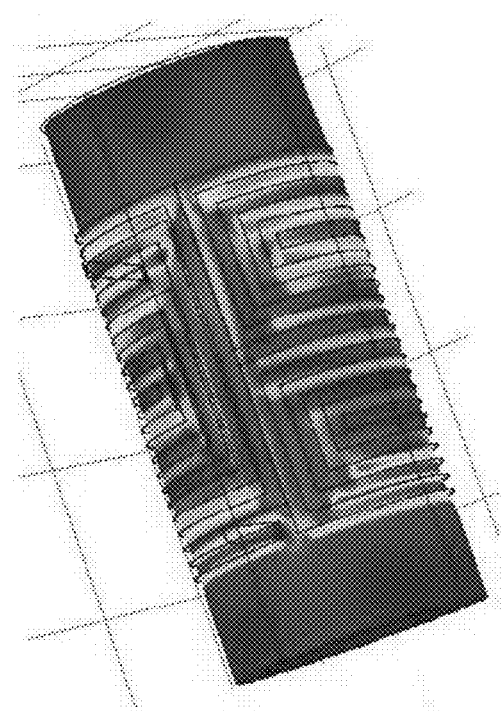
FIG. 7B is a simulated plot showing distribution of stress field in the flexible printed circuit of FIG. 5A wrapped in the first configuration.
Figure 7A:
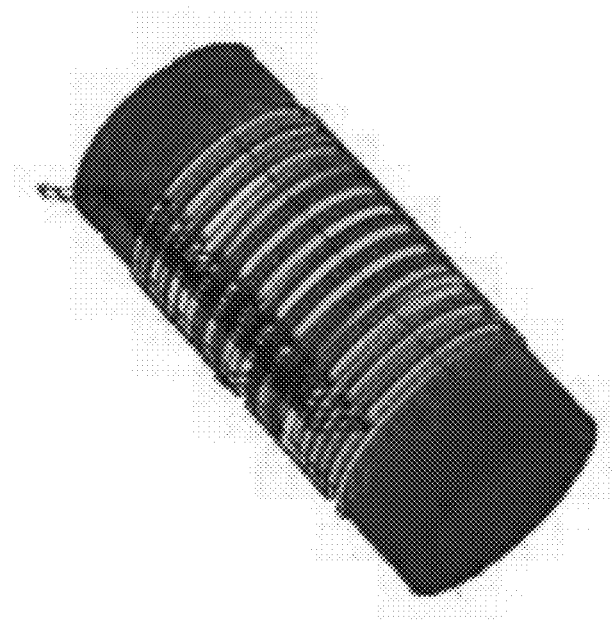
FIG. 7A is a simulated plot showing distribution of stress field in the flexible printed circuit of FIG. 5A wrapped in the second configuration.

FIGS. 7A and 7B are simulated plots showing distribution of stress field in the flexible printed circuit of FIG. 6A wrapped in the second configuration (FIG. 7A) and in the first configuration (FIG. 7B). Due to the uniform magnetic flux density generated by the second configuration, the stress it has induced is also much higher as illustrated in red colour in FIG. 7A. The non-uniform stress field and weakened stress induced by the first configuration can be observed in FIG. 7B.

As shown, the coil in the second configuration generates a more even stress distribution and higher stress level than that of the coil in the first configuration. The higher the stress level, the more the energy that the desired L mode guided-wave signal can be excited, and the longer the distance that the guided-wave signal can propagate along the pipe, and the higher the sensitivity in detecting small defect. Thus, the coil in the second configuration performs much better than the coil in the first configuration for defect detection in objects such as a pipe.

Figure 8B:
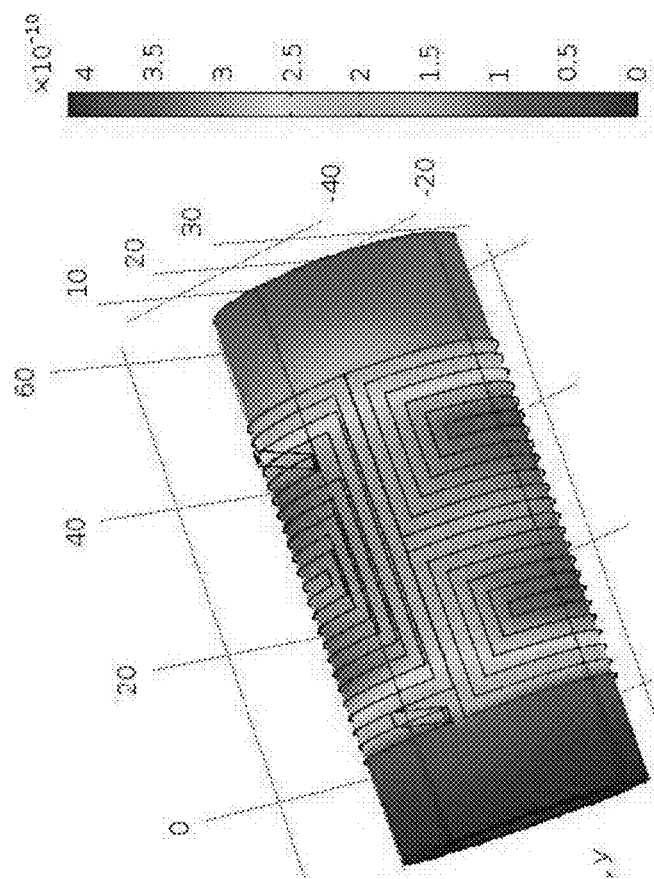
FIG. 8B is a simulated plot showing intensity of sensor displacement in the flexible printed circuit of FIG. 5A wrapped in the first configuration.
Figure 8A:
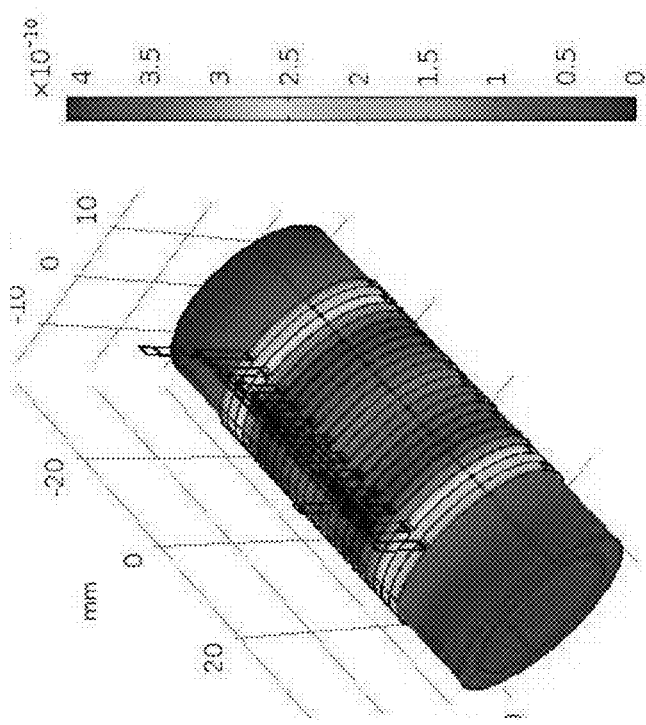
FIG. 8A is a simulated plot showing intensity of sensor displacement in the flexible printed circuit of FIG. 5A wrapped in the second configuration.

FIGS. 8A and 8B are simulated plots showing intensity of sensor displacement in the flexible printed circuit of FIG. 6A wrapped in the second configuration (FIG. 8A) and in the first configuration (FIG. 8B). As shown, the coil in the second configuration shows a much higher level of displacement as well as a more even distribution of displacement whereas the coil in the first configuration shows a smaller level of displacement and unevenly distribution of displacement. Since the higher the level of displacement, the larger the strength in exciting the desired elastic guided-wave signal, again, the coil in the second configuration outperforms the coil in the first configuration for defect detection.

Figure 9B:
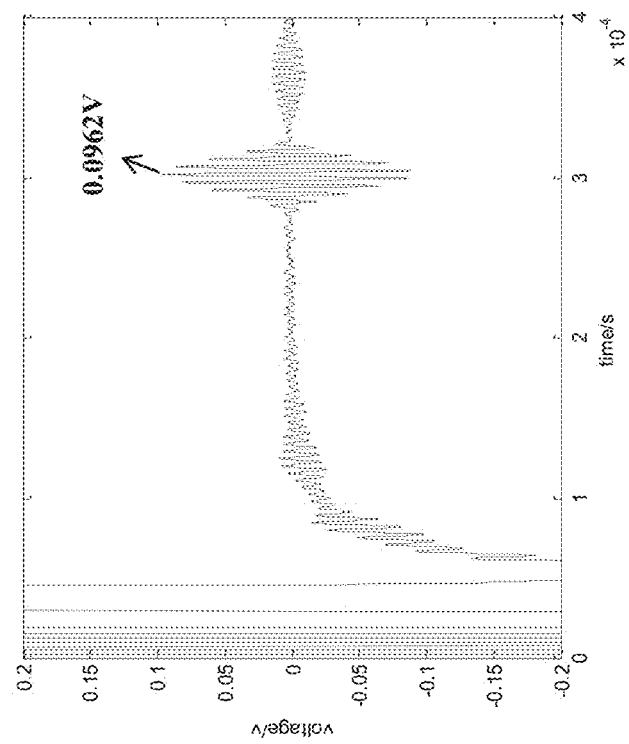
FIG. 9B is a graph showing experimental results of the amplitude of the guided-wave signal generated by reflection from a defect on a pipe for the flexible printed circuit of FIG. 5A wrapped in the first configuration.
Figure 9A:
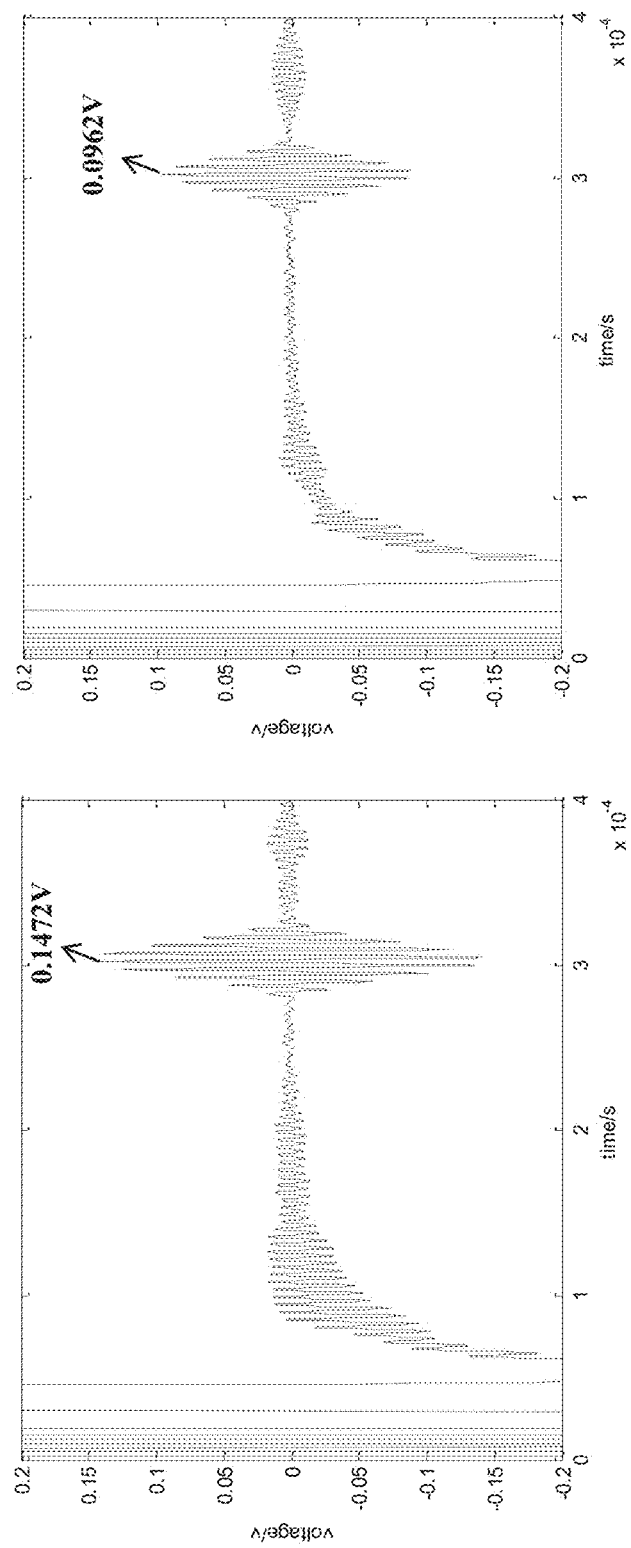
FIG. 9A is a graph showing experimental results of the amplitude of the guided-wave signal generated by reflection from a defect on a pipe for the flexible printed circuit of FIG. 5A wrapped in the second configuration.

FIGS. 9A and 9B are graphs showing experimental results of the amplitude of the guided-wave signal generated by reflection from a defect on a pipe when the flexible printed circuit of FIG. 6A wrapped in the second configuration (FIG. 9A) and in the first configuration (FIG. 9B). In the second configuration, the amplitude of guided-wave signal reflected by the defect is 0.1472V; in the first configuration, the amplitude of guided-wave signal reflected by the defect is 0.0962V. The second configuration represents a 53% increase in defect detection sensitivity over the first configuration.

Figures 10A, 10B:
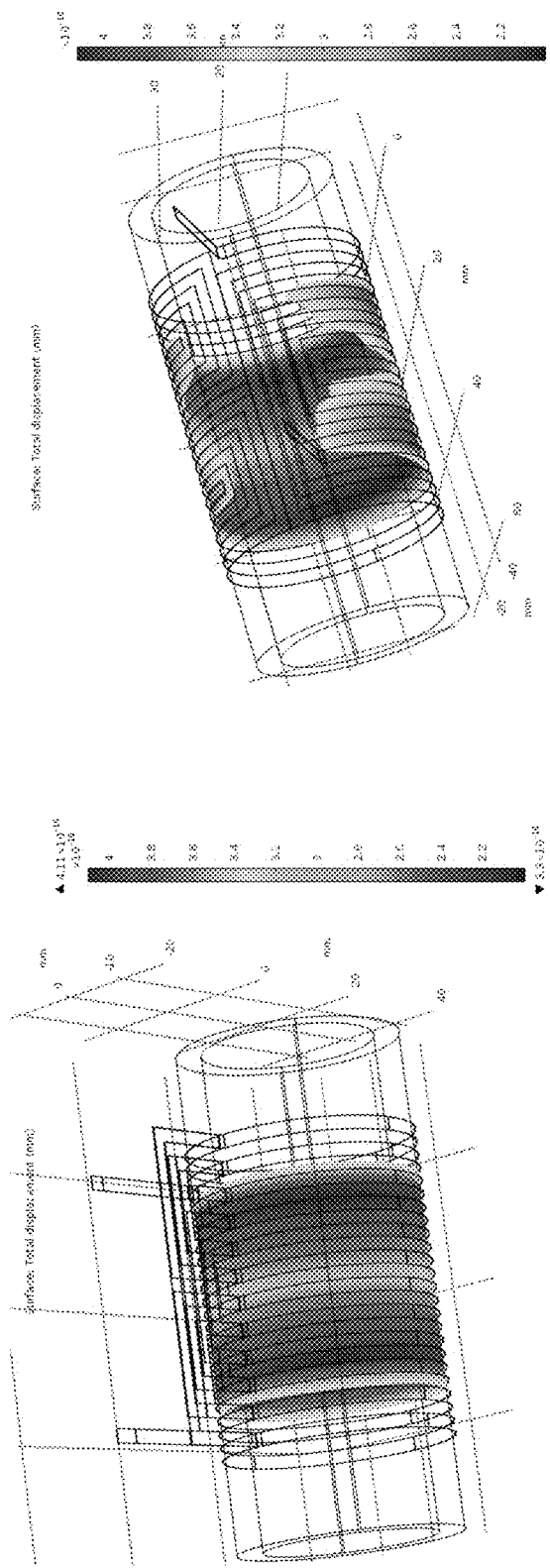
FIG. 10A is a graph showing experimental results of displacement area of the smart material patch surrounded by the flexible printed circuit of FIG. 5A wrapped in the second configuration.
FIG. 10B is a graph showing experimental results of displacement area of the smart material patch surrounded by the flexible printed circuit of FIG. 5A wrapped in the first configuration.

FIGS. 10A and 10B are graphs showing experimental results of displacement of the smart material patch surrounded by the flexible printed circuit of FIG. 5A wrapped in the second configuration (FIG. 10A) and in the first configuration (FIG. 10B), but only showing the portion with high displacement values. As seen, in the second configuration of FIG. 10A, the displacement area is evenly arranged around the smart material. In the first configuration of FIG. 10B, around 25% of the displacement area is lost.

Embodiments of the invention, the flexible printed coil or circuit in the second wrapped configuration, provides unique technical advantages. The coil in the second configuration provides not only uniform dynamic magnetic field, but also evenly distributed stress level and displacement, reduces the chance of creating undesirable mode conversion, such as the Flexural mode ("F-mode"), and also reduces noise. As a result, the received temporal guided-wave signals reflected by encountered cracks or corroded area will be properly detected, and the requirement on post-processing on the received guided-wave waveforms for analysis is lowered. In turn, the time information of each reflection can be determined easily, and the location of crack or the extent of each corroded area can be detected easily.

It has been shown that the flexible printed coil-based magnetostrictive sensor, with the coil in the second configuration, can provide a more uniform and even distribution of magnetic flux and magnetic field than when the coil is in the first configuration. As a result, such sensor with the coil in the second configuration is capable of inspecting longer pipes and detecting smaller defects. The sensor may also be used for detection of defect in situations which the object or structure to be inspected is partially covered by soil or concrete wall. With the help of the smart material layer, the magnetostrictive sensor can be used for inspection of both metal and plastic (e.g., PVC) pipes. The flexible printed coil, when in the second configuration, may also be suitable for wrapping around structures and objects of different sizes, avoiding the need to tailor-make coils for each specific structure and object in specific applications.

Although in the above description, the object to be inspected is a substantially cylindrical hollow pipe 20, such pipe is not the only application of the apparatus or system of the invention. In some embodiments, the object may be of other shapes, such as cuboidal, prismatic, cubical, etc. Also, the object may be any one of: a pipe, a tube, a rod, a strand, and a cable. The object may be made of plastic or metal. For example, the object may be drainage pipe, oil pipe, gas pipe, etc., in buildings, underground, oil fields, subsea area, etc.

Also, the flexible printed circuit or coil 100, 200, 400 in the invention may take a form or shape different from that in FIGS. 1A and 2A. For example, the flexible printed circuit may be a square sheet, a rounded sheet, a sheet of any regular or irregular shape. The first sections are not necessarily extending parallel to the first and second sides. The first section are not necessarily equally spaced. Instead of being a continuous strip, the conductor may be formed of multiple sections. The way how the conductor is routed may differ so long as the conductor contains first sections arranged adjacent and substantially parallel to each other, and each extending between the first and second ends. The conductor may include two or more first sections, and one or more second sections. The number of first and second sections need not correspond. The first and second sections may have the same or different thickness or width or height. The first sections need not be strictly linear so long as they have a general tendency to extend between the first and second ends. The conductors may be formed in a single layer or multi-layers. For example, multiple sheets of flexible printed circuit or coil 100, 200, 400 may be combined for form one circuit. More generally, the flexible printed circuit or coil includes a conductor arranged to receive an alternating current for generating magnetic field, and during operation when the flexible body attached to an object to be inspected, a first part of the conductor arranged to generate a magnetic field parallel to a longitudinal direction of the object is arranged to surround the object, and a second part of the conductor arranged to generate a magnetic field perpendicular to the longitudinal direction of the object is disposed away from (e.g., extend away from) the object.

It will be appreciated by persons skilled in the art that numerous other variations and/or modifications may be made to the invention as shown in the specific embodiments. The present embodiments are, therefore, to be considered in all respects as illustrative and not restrictive.

The invention claimed is:

1. An apparatus for a magnetostrictive sensor for guided-wave-based inspection, comprising:
   a flexible body with a conductor arranged to receive an alternating current for generating magnetic field,
   wherein during operation the flexible body is arranged to be attached to an object to be inspected in such a way that
   a first part of the conductor arranged to generate a magnetic field parallel to a longitudinal direction of the object is arranged to surround the object; and
   a second part of the conductor arranged to generate a magnetic field perpendicular to the longitudinal direction of the object is disposed away from the object.

2. The apparatus of claim 1, wherein
   the flexible body comprises first and second ends;
   the first part comprises a plurality of first sections arranged adjacent and substantially parallel to each other and each extending between the first and second ends; and
   the second part comprises at least one second section for connecting the plurality of first sections.

3. The apparatus of claim 2, wherein the plurality of first sections each extend at least 50% of a length between the first and second ends.

4. The apparatus of claim 2, wherein the conductor is a single, continuous conductor.

5. The apparatus of claim 2, wherein the plurality of first sections are spaced apart equally.

6. The apparatus of claim 2, wherein the plurality of first sections form at least two adjacent groups, each having at least one first section; wherein during operation when an alternating current is supplied to the conductor, current direction in the first sections of two adjacent groups are opposite.

7. The apparatus of claim 2, wherein the plurality of first sections form at least two adjacent groups, each having a plurality of adjacent first sections; wherein during operation when an alternating current is supplied to the conductor, current direction in the first sections of the same group is the same while current direction in the first sections of the two adjacent groups are opposite.

8. The apparatus of claim 7, wherein a width spanned by the first sections of each group is substantially the same.

9. The apparatus of claim 7, wherein a width spanned by the first sections of each group is equal to:

$$\frac{V_p}{2f_0}$$

where $f_0$ is a centre frequency of the magnetostrictive sensor, and $V_p$ is a phase velocity of an excited longitudinal guided-wave.

10. The apparatus of claim 2, the conductor comprises a plurality of second sections disposed at both the first and second ends.

11. The apparatus of claim 10, wherein each of the plurality of second sections comprises at least one part that extends generally perpendicular to the plurality of first sections.

12. The apparatus of claim 1, wherein the object is substantially cylindrical.

13. The apparatus of claim 1, wherein the object comprises any one of: a pipe, a tube, a rod, a strand, and a cable.

14. The apparatus of claim 1, wherein the flexible body comprises a flexible printed coil.

15. The apparatus of claim 1, further comprising a fastener arranged to hold the second part away from the object.

16. The apparatus of claim 1, wherein the flexible body is arranged to be wrapped around a smart material layer disposed on the object during operation in such a way that the first part surrounds the smart material layer and the second part is disposed away from the smart material layer.

17. The apparatus of claim 16, wherein the object is made of plastic or metal.

18. A system for use in guided-wave-based inspection, comprising:
a flexible smart material layer arranged to be attached to an object to be inspected;
an apparatus with a flexible body having a conductor arranged to receive an alternating current for generating magnetic field, wherein during operation the flexible body is to arranged to be attached to the smart material layer attached to the object in such a way that
a first part of the conductor arranged to generate a magnetic field parallel to a longitudinal direction of the smart material layer is arranged to surround the smart material layer; and
a second part of the conductor arranged to generate a magnetic field perpendicular to the longitudinal direction of the smart material layer is disposed away from the smart material layer.

19. The system of claim 18, wherein
the flexible body comprises first and second ends;
the first part comprises a plurality of first sections arranged adjacent and substantially parallel to each other, each extending between the first and second ends; and
the second part comprises at least one second section for connecting the plurality of first sections.

20. The system of claim 18, further comprising a magnetic field generator for generating a static magnetic field in one or both of the object to be inspected and the smart material layer.

21. The system of claim 18, further comprising a fastener arranged to hold the second part away from the smart material layer.

22. The system of claim 18, further comprising a data acquisition unit arranged to be connected with the smart material patch for acquiring detection signals received.

23. The system of claim 18, wherein the flexible body comprises a flexible printed coil.

24. The system of claim 18, wherein the object is substantially cylindrical and comprises any one of: a pipe, a tube, a rod, a strand, and a cable.

25. A method for guided-wave-based inspection, comprising the steps of:
providing an apparatus for a magnetostrictive sensor for guided-wave-based inspection, comprising a flexible body with a conductor arranged to receive an alternating current for generating magnetic field; and
attaching the flexible body to an object to be inspected in such a way that
a first part of the conductor arranged to generate a magnetic field parallel to a longitudinal direction of the object is arranged to surround the object and
a second part of the conductor arranged to generate a magnetic field perpendicular to the longitudinal direction of the object is disposed away from the object.

26. The method of claim 25, further comprising the step of:
attaching a flexible smart material layer to the object to be inspected prior to attaching the flexible body to the object.

* * * * *